(12) United States Patent
Haupt

(10) Patent No.: US 10,835,202 B2
(45) Date of Patent: Nov. 17, 2020

(54) SYSTEM AND METHOD FOR ANALYZING TISSUE USING SHEAR WAVES

(71) Applicant: Massachusetts Institute of Technology, Cambridge, MA (US)

(72) Inventor: Robert W. Haupt, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 834 days.

(21) Appl. No.: 14/538,040

(22) Filed: Nov. 11, 2014

(65) Prior Publication Data

US 2015/0148675 A1 May 28, 2015

Related U.S. Application Data

(60) Provisional application No. 61/908,059, filed on Nov. 23, 2013.

(51) Int. Cl.
*A61B 8/08* (2006.01)
*G01S 7/52* (2006.01)
(Continued)

(52) U.S. Cl.
CPC .......... *A61B 8/0808* (2013.01); *A61B 5/0051* (2013.01); *A61B 5/0059* (2013.01); *A61B 8/08* (2013.01); *A61B 8/085* (2013.01); *A61B 8/0875* (2013.01); *A61B 8/485* (2013.01); *A61B 8/488* (2013.01); *A61B 8/5215* (2013.01); *A61B 8/5223* (2013.01); *G01N 29/0654* (2013.01); *G01S 7/52042* (2013.01); *G01S 15/8913* (2013.01); *G01S 15/8915* (2013.01);
(Continued)

(58) Field of Classification Search
CPC ... A61B 8/0808; A61B 5/0051; A61B 5/0059; A61B 8/08; A61B 8/085; A61B 8/0875; A61B 8/485; A61B 8/488; A61B 8/5215; A61B 8/5223; G01N 29/0654; G01S 7/52042; G01S 15/8913; G01S 15/8915
See application file for complete search history.

(56) References Cited

U.S. PATENT DOCUMENTS 3,512,400 A * 5/1970 Lynnworth .......... G01N 29/043
73/597
4,218,924 A * 8/1980 Fortunko ........... G01N 29/2412
73/642

(Continued)

OTHER PUBLICATIONS

Urban et al., "A Review of Shearwave Dispersion Ultrasound Vibrometry (SDUV) and its Applications", Current Medical Imaging Reviews, vol. 8, No. 1, 2012, pp. 27-36.*

(Continued)

*Primary Examiner* — Katherine L Fernandez
*Assistant Examiner* — Colin T. Sakamoto
(74) *Attorney, Agent, or Firm* — Quarles & Brady LLP

(57) ABSTRACT

A system and method for determining tissue changes. Shear waves are transmitted across the tissue in response to an ultrasonic signal input exterior to the tissue surface. Adaptive beam forming signal processing is applied to signal returns and arrivals to remove distortions by targeting velocity contrasts. Shear-wave dispersion, such as due to viscosity and mass changes in the tissue, are then estimated and compared to reference data to determine tissue health.

22 Claims, 12 Drawing Sheets

(51) Int. Cl.
  *G01S 15/89* (2006.01)
  *A61B 5/00* (2006.01)
  *G01N 29/06* (2006.01)
  *G01N 29/11* (2006.01)
  *G01N 29/34* (2006.01)
  *A61B 5/055* (2006.01)

(52) U.S. Cl.
  CPC ............ *A61B 5/055* (2013.01); *A61B 8/0858* (2013.01); *G01N 29/11* (2013.01); *G01N 29/346* (2013.01); *G01N 2291/02475* (2013.01); *G01N 2291/02491* (2013.01); *G01N 2291/02827* (2013.01); *G01N 2291/0422* (2013.01); *G01S 7/52047* (2013.01)

(56) References Cited

U.S. PATENT DOCUMENTS

| | | | | |
|---|---|---|---|---|
| 4,522,071 A * | 6/1985 | Thompson | ............ | G01N 29/07 73/597 |
| 4,554,836 A * | 11/1985 | Rudd | ............ | G01H 9/00 73/657 |
| 5,154,081 A * | 10/1992 | Thompson | ............ | G01N 29/07 73/597 |
| 5,629,485 A * | 5/1997 | Rose | ............ | B64D 15/20 73/170.26 |
| 5,804,727 A * | 9/1998 | Lu | ............ | G01H 5/00 73/159 |
| 5,810,731 A * | 9/1998 | Sarvazyan | ............ | A61B 8/08 600/438 |
| 2010/0010346 A1* | 1/2010 | Greenleaf | ............ | A61B 5/0051 600/438 |
| 2010/0058869 A1* | 3/2010 | Cawley | ............ | G01N 29/069 73/596 |
| 2011/0130660 A1* | 6/2011 | Cloutier | ............ | A61B 5/02007 600/438 |
| 2012/0063266 A1* | 3/2012 | Hardage | ............ | G01V 1/284 367/43 |
| 2012/0108968 A1* | 5/2012 | Freiburger | ............ | A61B 8/0825 600/443 |
| 2014/0046173 A1* | 2/2014 | Greenleaf | ............ | G01N 21/17 600/411 |

OTHER PUBLICATIONS

Shung, "Diagnositic Ultrasound: Imaging and Blood Flow Measurements". 2006.*

* cited by examiner

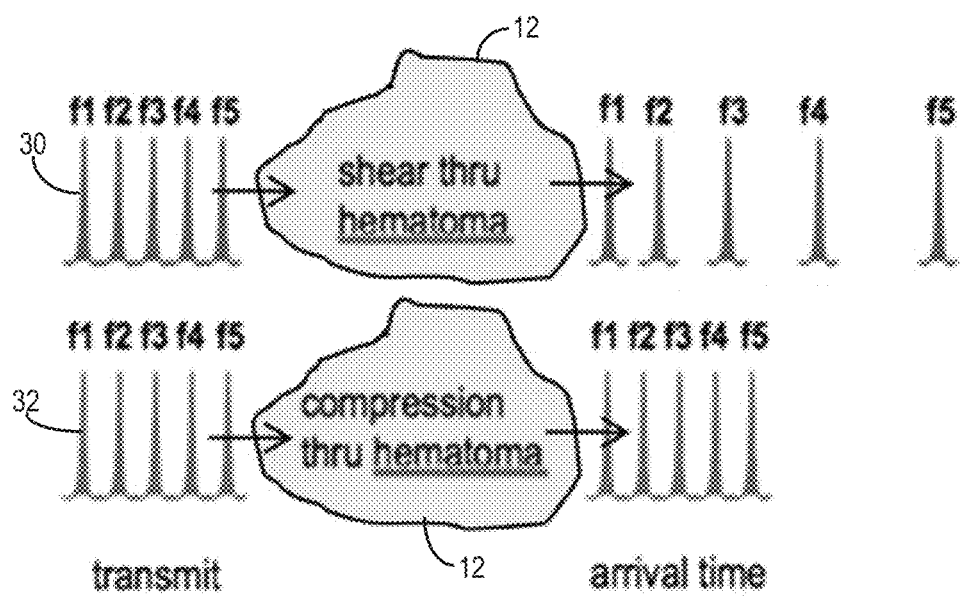
FIG. 6
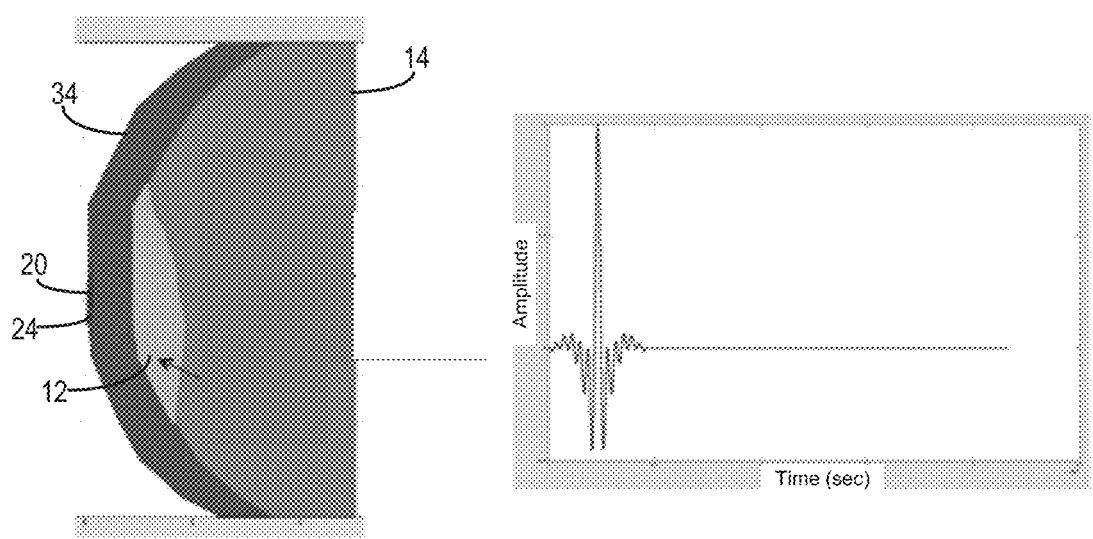
FIG. 7A                    FIG. 7B

SYSTEM AND METHOD FOR ANALYZING TISSUE USING SHEAR WAVES

CROSS-REFERENCE TO RELATED APPLICATIONS

This application is based on, claims priority to, and incorporates herein by reference in its entirety U.S. Provisional Application Ser. No. 61/908,059, filed Nov. 23, 2013, and entitled, "SYSTEM AND METHOD FOR ANALYZING TISSUE USING SHEAR WAVES."

STATEMENT REGARDING FEDERALLY SPONSORED RESEARCH

This invention was made with government support under FA8721-05-C-0002 awarded by the Air Force Life Cycle Management Center. The government has certain rights in the invention.

BACKGROUND

The present disclosure relates to systems and methods for analyzing tissue health, and more particularly to systems and methods for analyzing tissue using shear waves that propagate through tissue.

Internal injury such as traumatic brain injury (TBI), stress induced bone fracturing from carrying heavy loads, for example, and internal organ bleeding from concussive impacts can be life threatening or require long term rehabilitation. These injuries often show no apparent physical symptoms when examined by field medical personnel and remain undetected until the injury advances to a more serious state. Performing medical diagnostics for civilians and the war fighter in the field, for example, to determine if serious internal injury has occurred, and if the patient needs to be moved quickly to a hospital for further evaluation and treatment is often challenging.

Ultrasonic imaging techniques of body tissue and bone are well established in medical practices and aid physicians in diagnosing diseases and injuries. Recent advances in medical ultrasonic imaging exploit shear-wave dispersion phenomena to measure abnormal viscosity changes in organ tissues. However, viscosity abnormalities can be caused by contusion and blood coagulation resulting from internal bleeding and hemorrhaging experienced by TBI and concussive damage to organs. Thus, transcranial ultrasonic imaging is a challenging problem and more sophisticated approaches need to be investigated to overcome limitations of conventional ultrasonic imaging techniques. In other applications, bone stress-fracture fields and bone mass changes can reduce travel speeds and augment attenuation and scattering of shear-waves relative to healthy bone structure. However, conventional ultrasonic imaging approaches may not effectively detect and image these defects.

Thus, there is a need for systems and methods capable of providing clinical feedback for the diagnosis and, thereby, treatment of potential injuries that provide little or no indication or apparent injury at the surface of the patient, such as TBI and bone fractures.

SUMMARY

The present disclosure provides system and methods that overcome the aforementioned drawbacks by providing ultrasonic acquisition configurations and processing methods that exploit shear-waves to detect and image internal damage from concussive and load-bearing injuries, for example. The present disclosure may use transverse, horizontal sources that do not create significant surface waves in the direction of propagation, and uses transverse horizontal receivers that can measure the predominant transverse shear wave. Additionally, the present disclosure provides ultrasonic transducer and sensor acquisition configurations that reduce clutter interference with desired shear-wave signals, and implements adaptive beam-forming signal processing techniques that compensate for the effects of complex heterogeneity in body tissue and bone on ultrasonic wave propagation.

The present disclosure provides a method for determining changes in tissue. The steps of the method include positioning an ultrasonic wave excitation source exterior to the tissue to provide an ultrasonic signal input. An ultrasonic receiver array is positioned at an offset distance from the ultrasonic wave excitation source exterior to the tissue to receive signal returns and arrivals from the ultrasonic wave excitation source. Adaptive beam forming signal processing is applied to the signal returns and arrivals to remove distortions by targeting velocity contrasts caused by heterogeneity in the tissue. Shear-wave dispersion due to viscosity changes in the tissue or mass changes in the tissue may be estimated using the signal returns and arrivals. A report is then generated indicative of the tissue health based on either the viscosity changes or the mass changes.

The present disclosure also provides a system for determining changes in tissue. The system includes an ultrasonic wave excitation source configured to be positioned exterior to the tissue to provide an ultrasonic signal input. The system also includes an ultrasonic receiver array configured to be positioned at an offset distance from the ultrasonic wave excitation source and exterior to the tissue to receive signal returns and arrivals from the ultrasonic wave excitation source. A data acquisition system is configured to acquire the signal returns and arrivals at the ultrasonic receiver array. The system further includes a processor that has access to the data acquisition system. The processor is configured to apply adaptive beam forming signal processing to the signal returns and arrivals to control distortions by targeting velocity contrasts caused by heterogeneity in the tissue. In addition, the processor is configured to estimating shear-wave dispersion due to viscosity changes in the tissue or mass changes in the tissue. The processor may then generate a report indicative of tissue health based on the viscosity changes or the mass changes.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 6 is a diagram illustrating shear waves and compression waves being transmitted through a hematoma.

FIG. 7A is a diagram illustrating shear wave transmission across a skull-brain interface having a hematoma in response to an ultrasonic signal input.

FIG. 7B is a graph showing the amplitude of the ultrasonic signal input of FIG. 7A over time.

DETAILED DESCRIPTION

The complex heterogeneity of the body structure has significant effects on the transmission speeds and attenuation of elastic waves that are used to image the body. Soft tissues, for example, exhibit elastic wave velocities on the order of 1500 m/s, while bone, for example, exhibits velocities a factor of two or greater. These velocity contrasts produce distortions in the resulting ultrasonic image, thus, reducing resolution and location accuracy. Correcting image distortions is not easily accomplished through predictive methods since the heterogeneity distribution varies in individual bodies and from person to person. Determining the heterogeneity distribution in-situ by empirical measurement yields an approach to obtain higher resolution and more accurate location within the limits of the ultrasonic wavelength. Thus, adaptive beam forming signal processing, as will be described in further detail below, from an array of ultrasonic receivers can provide the necessary corrections required for ultrasonic images.

Additionally, exploiting the polarity of the ultrasonic excitation source and receivers can significantly mitigate signal interference from the host of unwanted surface, body, and converted waves that are created during conventional ultrasonic excitation processes. As a result, the signal returns from the target (i.e., hematomas) can yield a high signal to noise ratio (SNR) and more resolved images. In addition, surface waves are typically dominant over standard compressional wave sources and exhibit retrograde-elliptical particle motions in the direction of wave propagation. When looking for shallow targets, as in the case of hematomas just under the skull in traumatic brain injury (TBI), induced surface waves can interfere with the compressional wave returns of interest and cannot be time gated out.

Figure 1:
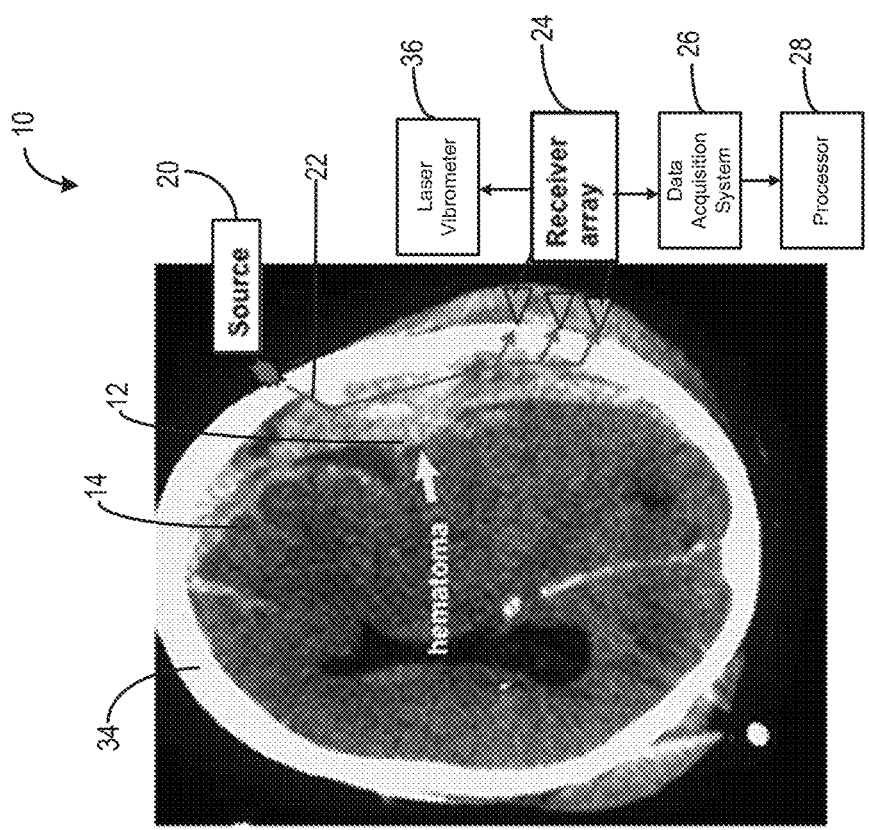
FIG. 1 is a schematic diagram of a system configured to implement the present disclosure for imaging the presence of a hematoma.

Referring now to FIG. 1, a system 10 is shown that may exploit reflected and refracted body waves and direct surface waves to estimate shear-wave dispersion due to blood viscosity changes in hematomas 12 in brain tissue 14, for example, compared to reference data. The reference data, may be ultrasonic images of healthy tissue, for example, or prior ultrasonic images of a patient's tissue. In addition, referring to FIG. 2, the system 10 may also use direct wave propagation amplitude and phase variations to determine fractures 16 and mass changes in bone 18, for example; however, other tissue may be examined to determine viscosity and mass changes using the system 10 shown in FIGS. 1 and 2.

As shown in FIG. 1, the system 10 may include an ultrasonic wave excitation source 20 configured to be positioned exterior to brain tissue 14 to deliver an ultrasonic signal input 22. The ultrasonic wave excitation source 20 may be a transverse or horizontal source. For example, the ultrasonic wave excitation source 20 may include a set of piezoelectric ultrasonic transducers used as contact sources placed on the exterior surface of the brain tissue 14, such as externally to a skull 34 surrounding the brain tissue 14. The transducers may consist of one inch diameter stacks, for example, that have the ability to couple ultrasonic shear waves in either the transverse or inline directions and compressional waves in the vertical direction. The transducers can generate frequencies over a broad band, for example, ranging from 10 kHz to 1 MHz.

An ultrasonic receiver array 24 may be positioned at an offset distance from the ultrasonic wave excitation source 20, also exterior to the brain tissue 14. The ultrasonic receiver array 24 may be, for example, a set of sixteen ultrasonic receivers to process focused images based on normal hyperbolic move-out to estimate travel velocities in the tissue. The ultrasonic wave excitation source 20 and the ultrasonic receiver array 24 may be oriented to mitigate interference from unwanted surface and body waves. The ultrasonic receiver array 24 may be configured to receive signal returns and arrivals from the ultrasonic wave excitation source 20.

A data acquisition system 26, for example an IOTECH Wavebook recording system, may be coupled to the ultrasonic receiver array 24 and configured to acquire the signal returns and arrivals. The signal returns and arrivals may include, for example, the reflected and refracted body waves and direct surface waves induced by the ultrasonic wave excitation source 20 and received at the ultrasonic receiver array 24. The signal returns and arrivals may then be processed by a processor 28 having access to the data acquisition system 26. The processor 28 may be configured to measure shear-wave transmission across the brain tissue 14 in response to the ultrasonic signal input 22. The processor 28 may then apply adaptive beam forming signal processing, as will be described in further detail below, to the signal returns and arrivals to remove distortions by targeting velocity contrasts caused by heterogeneity in the brain tissue 14. Shear-wave dispersion due to viscosity changes in the brain tissue 14 may be estimated and compared to the reference data. The viscosity in the hematoma 12 may generate a shear wave dispersion that differs from the reference data. The processor 28 may then generate a report indicative of the tissue health of the brain tissue 14 compared to the reference data. Therefore, the report may indicate the likelihood of traumatic brain injury or internal bleeding, for example, based on the comparison to the reference data.

Figure 2:
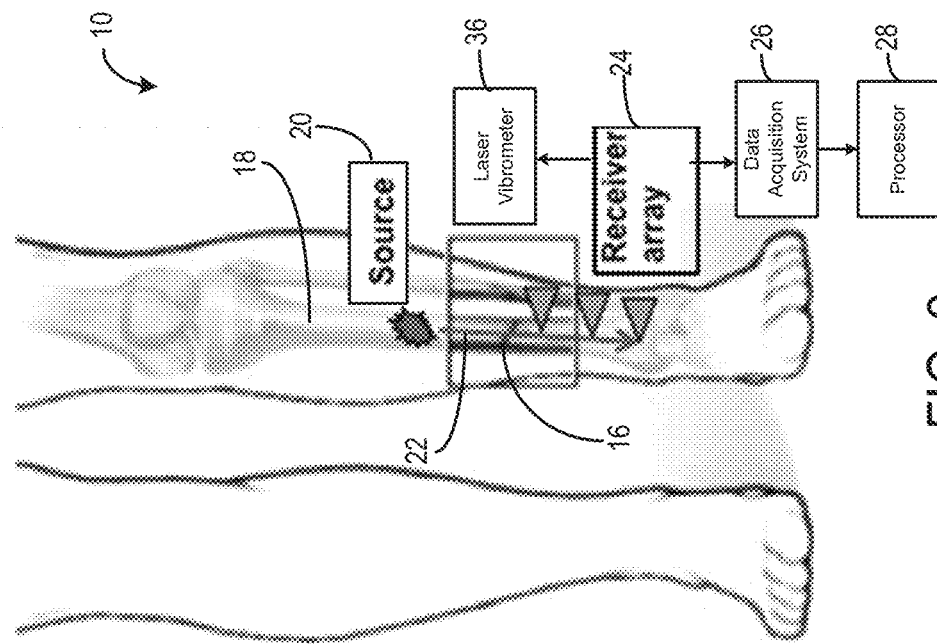
FIG. 2 is a schematic diagram of the system of FIG. 1 configured for imaging the presence of a bone fracture.

Similarly, as shown in FIG. 2, the ultrasonic wave excitation source 20 may be positioned exterior to the bone 18 to provide the ultrasonic signal input 22 directed to the bone 18. As described above, the ultrasonic wave excitation source 20 may be a transverse, horizontal source, for example. The ultrasonic receiver array 24 may be positioned at an offset distance from the ultrasonic wave excitation source 20 exterior to the bone 18. The ultrasonic receiver array 24 may be configured to receive signal returns and arrivals from the ultrasonic wave excitation source 20. As described, the data acquisition system 26 may be coupled to the ultrasonic receiver array 24 configured to acquire the signal returns and arrivals. The signal returns and arrivals may include, for example, the reflected and refracted body waves and direct surface waves induced by the ultrasonic wave excitation source 20 and received at the ultrasonic receiver array 24. The signal returns and arrivals may then be processed by the processor 28 having access to the data acquisition system 26.

The processor 28 may be configured to measure amplitude and phase variations of the direct surface wave propagation across the bone 18 to detect bone fracture 16 and bone density variations. As will be described, the processor 28 may then apply adaptive beam forming signal processing to the signal returns and arrivals to remove distortions by targeting velocity contrasts caused by heterogeneity in the bone 18. Shear-wave dispersion due to mass changes and viscosity changes, for example, in the bone 18 may be estimated and compared to the reference data. The direct surface waves and body shear-waves may be impeded by the fracture 16 compared to the reference data. The processor 28 may then generate a report indicative of the tissue health of the bone 18 compared to the reference data. Therefore, the report may indicate the likelihood of stress induced fracturing based on the comparison to the reference data.

In an alternative embodiment, the ultrasonic wave excitation source 20 and the ultrasonic receiver array 24 may be, for example, handheld transmitters and receivers that do not physically contact the exterior surface of the patient. The ultrasonic wave excitation source 20 may be, for example, focused ultrasonic forcing transducers that are non-contact excitation sources.

In addition a laser vibrometer 36 may be incorporated into the system 10, as shown in FIGS. 1 and 2, to provide a highly sensitive, non-contact method to measure the vibration field on the skin up to 10 MHz, for example, resulting from the ultrasonic wave excitation source 20. The ultrasonic vibration may modulate the laser receiver carrier and cause a Doppler shift as the skin surfaces vibrate towards and away from the laser vibrometer 36. The Doppler shift may provide the vibration frequency while the excursion across the number of wavelengths on the laser receiver carrier provides the signal amplitude. Vibration frequencies may be measured up to 2.5 MHz, for example, using commercial vibrometer systems, such as a Polytec, OFV 5000 or OFV 5005. The laser spot size can be adjusted to 1-mm diameter that provides a 1-mm position accuracy.

Figure 3A:
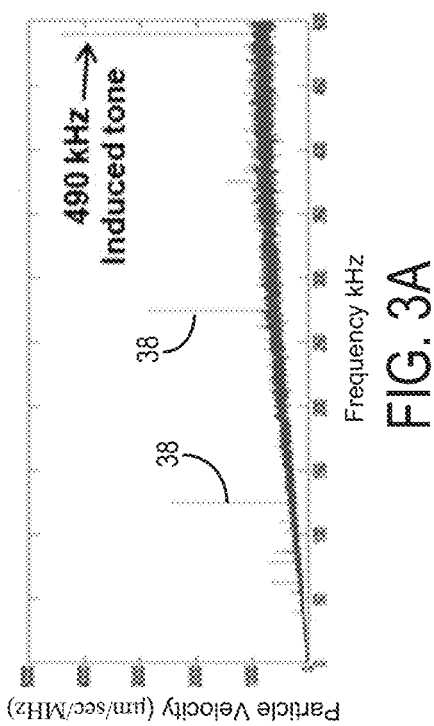
FIG. 3A is a graph showing particle velocity using a laser vibrometer to measure surface vibrations.
Figure 3B:
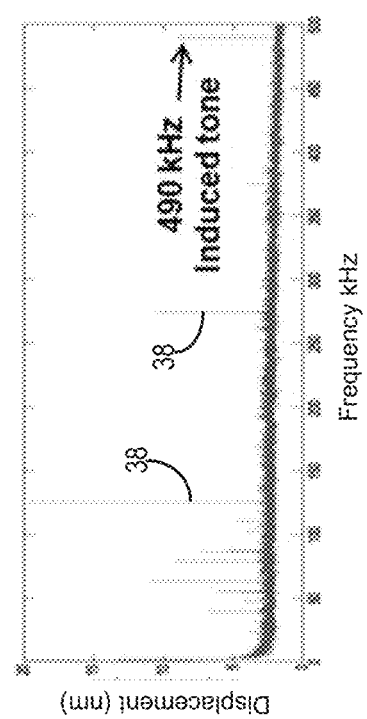
FIG. 3B is a graph showing displacement of ultrasonic elastic waves using the laser vibrometer.

In one non-limiting example, the laser vibrometer 36 may be a LVID laser vibrometer that incorporates a non-contact laser-ultrasound approach to measure surface vibrations caused by elastic longitudinal and shear waves that probe the body interior. Laser vibrometer measurements of surface vibrations may be acquired by contact ultrasonic transducers biological tissues. In some embodiments, the laser vibrometer 36 may be operated without any tissue surface preparation (e.g., such as gels, reflection enhancing materials, and the like). In use, CW vibrations may be excited into the tissue using, for example, any suitable ultrasonic transducer having a useable bandwidth from 300 kHz-1 MHz. As shown in FIG. 3A, the laser vibrometer 36 measured excitation tones 38 at different pointing spot locations over several centimeters from the excitation point. As shown in FIG. 3B, the vibrometer noise floor was approximately 5 nanometers in displacement. Thus, a laser vibrometer may be a suitable measurement device for ultrasonic elastic waves used in body tissue imaging.

Figure 4:
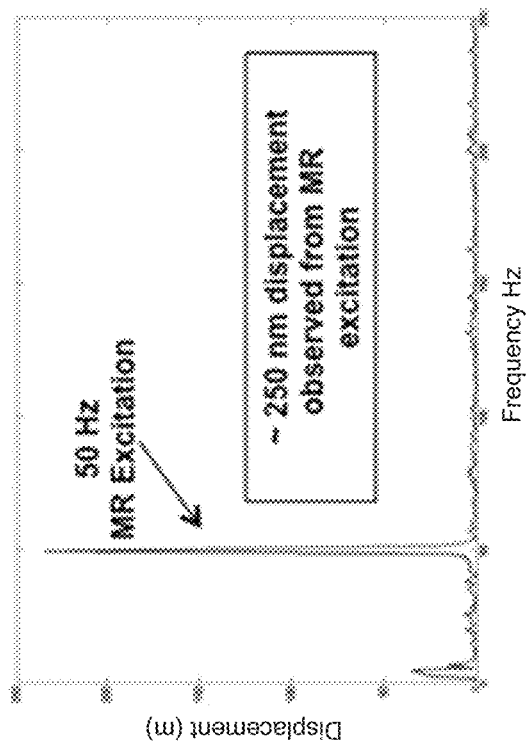
FIG. 4 is a graph showing displacement of ultrasonic elastic waves using MR elastography.

In yet another non-limiting example, the laser vibrometer 36 may be used to acquire elastography measurements, as shown in FIG. 4. Elastography is an established measurement technique that may be used to help detect and diagnosis certain forms of cancer, particularly tumors found in the body. Elastography works by inducing a low frequency shear wave via a horizontal shaker applied to the patient. An MRI scanner then measures the volumetric response distributed throughout the test volume, for example, looking for a tumor in a breast. Tumors are typically mechanically stiffer than healthy tissue (being very compliant in comparison) and exhibit a strong shear signal in that region. In one example, a LVID laser vibrometer may be positioned about 6 to 8 meters from the MRI target area to measure the excitation tone on the surface of the tissue. Thus, laser vibrometry may be used to measure vibrational phenomena associated with medical applications.

Figure 5:
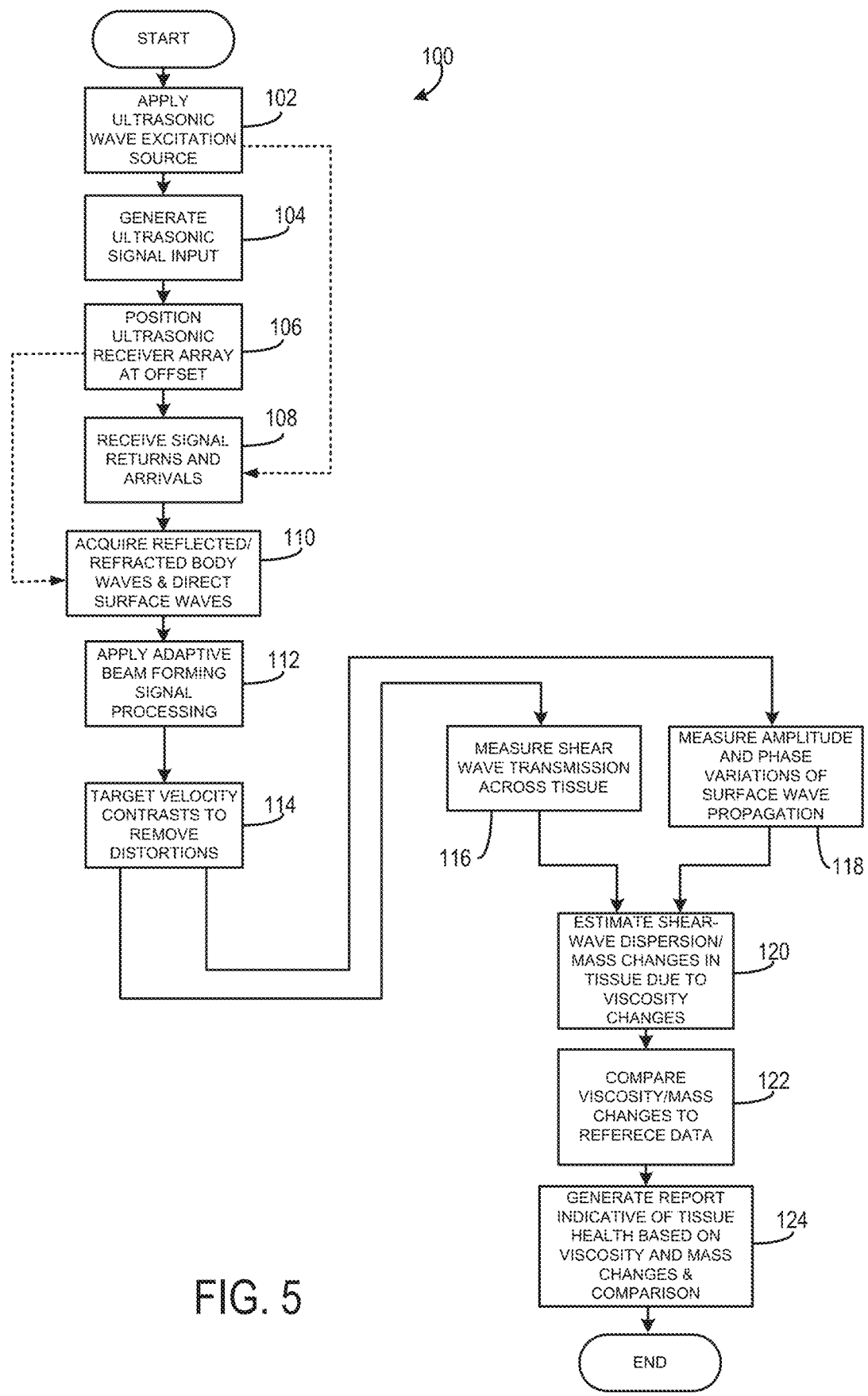
FIG. 5 is a flow chart setting forth the steps of processes for determining viscosity and mass changes in tissue in accordance with the present disclosure.

Referring now to FIG. 5, a flow chart setting forth exemplary steps 100 of a method for determining viscosity and mass changes in tissue is provided. At process block 102, the ultrasonic wave excitation source is applied to the exterior of the patient, such as the brain tissue 14 or bone 18 described above with respect to FIGS. 1 and 2, respectively, and, at process block 104, an ultrasonic signal input is generated. At process block 106, the ultrasonic receiver array is positioned at an offset with respect to the ultrasonic wave excitation source. Notably, in practice, the ultrasonic receiver array may be located in an initial position before the ultrasonic signal input is generated at process block 104; however, the ultrasonic receiver array and/or ultrasonic wave excitation source may be moved or adjusted during operation. In any case, at process block 108, the ultrasonic receiver array receives the signal returns and arrivals from the ultrasonic wave excitation source. At process block 110, the ultrasonic receiver array acquires reflected body wave, refracted body wave and direct surface wave induced by the ultrasonic wave excitation source 20 at process block 102.

At process block 112, adaptive beam forming signal processing may be applied to the signal returns and arrivals. In general, the adaptive beam forming signal processing may be performed to control distortions by targeting velocity contrasts at process block 114 that are caused by heterogeneity in the tissue. Adaptive beam forming algorithms may also be applied to the signal returns and arrivals to improve image SNR and to correct for travel speed variations and attenuation. In addition, predictive filters, such as deconvolution, can be applied to reduce reverberations and multiple reflections caused by large impedances between bone and tissue Once the reflected and refracted body waves and direct surface waves have been processed by the adaptive beam forming signal processing at process block 112, additional processing may be performed to provide information relevant to a particular clinical application. As illustrated, at process block 116 shear wave transmission across tissue may be measured. In the case of studying the brain tissue, for example, the shear-wave transmission across the brain tissue can be measured to determine the presence of, for example, a hematoma in response to the ultrasonic signal input. Also, as illustrated at process bock 118, amplitude and phase variations of surface wave propagation may be measured. In the case of studying bone, for example, the amplitude and phase variations of the direct surface wave propagation using the signal returns and arrivals can be measured to determine the presence of a bone fracture.

With continued reference to FIG. 5, at process block 120, the shear-wave dispersion due to viscosity changes in the brain tissue, for example, may be estimated and mass changes may be estimated in the bone, for example. As shown in FIG. 6, shear waves 30 exhibit velocity speed dispersion over frequency due to viscosity changes in coagulating blood associated with the hematoma 12. In other words, shear waves 30 disperse in hematomas 12 and the fluid viscosity increases due to coagulation. Thus, the shear modulus becomes non-zero and is frequency dependent. However, shear waves 30 may not be present in healthy brain tissue or un-coagulated blood; therefore, shear-wave dispersion may be used in the system to determine presence of a hematoma 12, for example, in brain tissue. This is advantageous over conventional ultrasound imaging modes, where compression waves 32, as shown in FIG. 6, are unlikely to sense hematomas 12 and stress fractures due to the constant frequency. Referring again to FIG. 5, the viscosity changes and the mass changes may be compared to reference data at process block 122 to generate a report indicative of the tissue health at process block 124.

Turning now to FIGS. 7A and 7B, an exemplary skull bone 34 and brain tissue 14 are shown with the presence of a hematoma 12. Shear waves are transmitted across the skull bone 34 and brain tissue 14 in response to the ultrasonic signal input 22 generated by the ultrasonic wave excitation source 20. The ultrasonic wave excitation source 20 and the ultrasonic receiver array 24 are positioned exterior to the brain tissue 14, as shown in FIG. 7A. The amplitude of the ultrasonic signal input increases as shown in the graph in FIG. 7B, as it transmits through the hematoma 12.

Figure 8A:
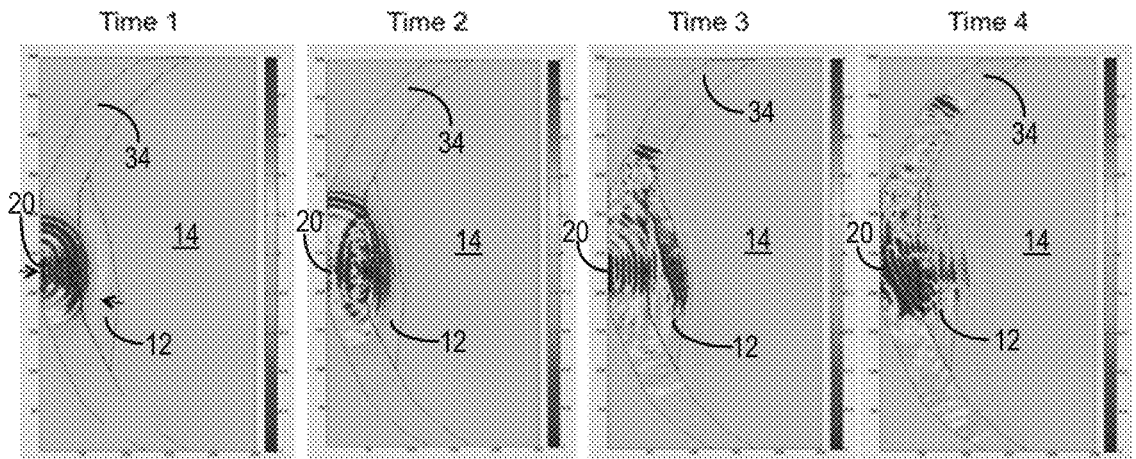
FIG. 8A is a set of images showing the shear wave transmission and propagation across the skull-brain interface of FIG. 7A and the effects of the hematoma over time.
Figure 8B:
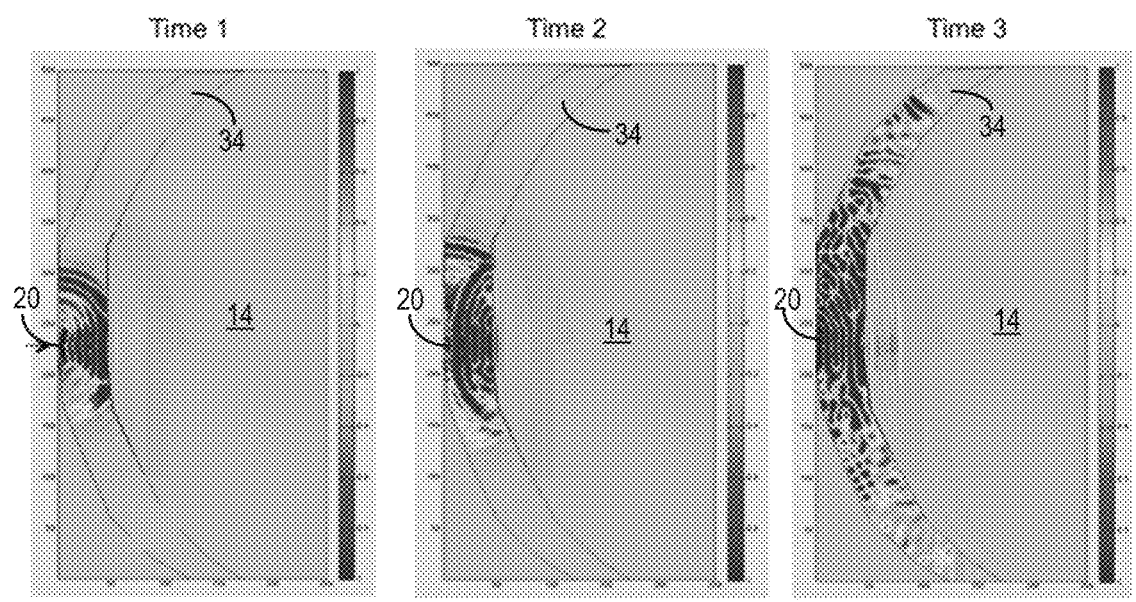
FIG. 8B is a set of images showing the shear wave transmission and propagation across the skull-brain interface and the effects of no hematoma present over time.

As shown in FIGS. 8A and 8B, shear wave transmission across skull bone 34 and brain tissue 14 in response to an ultrasonic signal input generated by the ultrasonic wave excitation source 20 positioned at the an exterior surface of the skull bone 34. Effects of the hematoma 12 are observed in the images over time and shows that hematoma viscosity is larger in FIG. 8A than that of healthy brain tissue as shown in FIG. 8B. Further, the hematoma 12 generates a significant reflected signal return that propagates to the skull 34 exterior surface, as shown in FIG. 8A, whereas no significant reflected ultrasonic signals return to the skull 34 exterior from inside the healthy brain tissue 14, as shown in FIG. 8B.

Figure 9A:
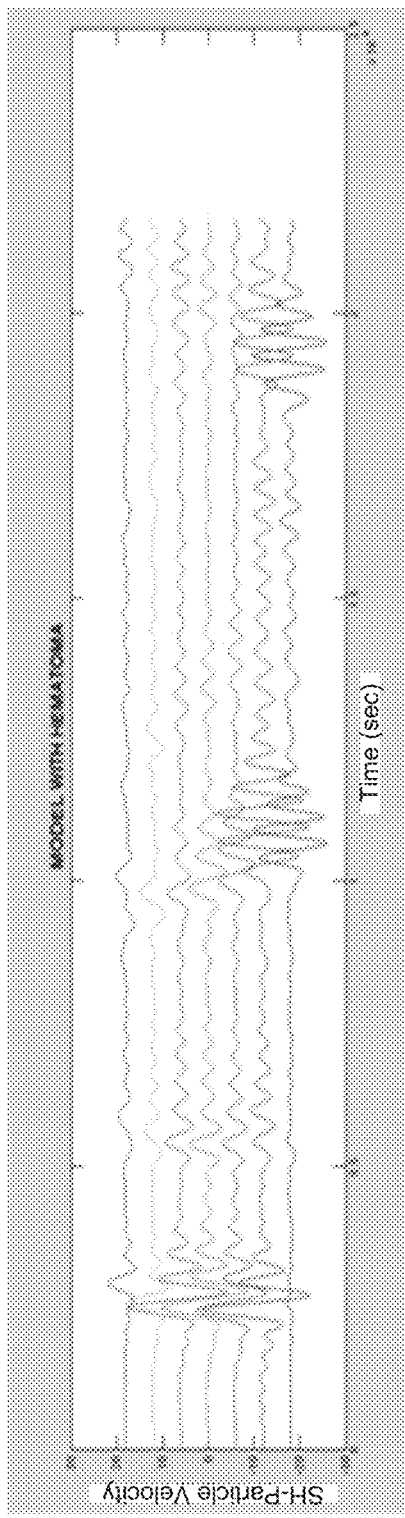
FIG. 9A is a graph showing the shear wave particle velocity as the shear waves are transmitted across a skull-brain interface and the effects of the hematoma over time.
Figure 9B:
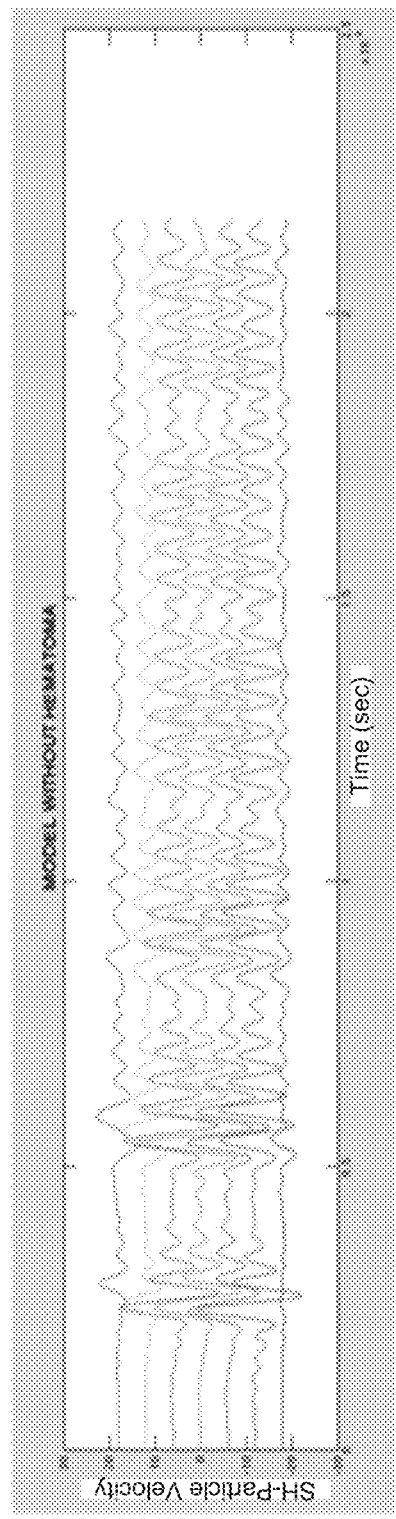
FIG. 9B is a graph showing the shear wave particle velocity as the shear waves are transmitted across a skull-brain interface and the effects of no hematoma present over time.

FIGS. 9A and 9B show shear wave transmission across the skull bone and brain tissue in response to the ultrasonic signal input at the skull exterior surface. The graphs show the time series of the ultrasonic receiver array, positioned at the exterior of the skull, that records signal returns from the skull-brain interface, skull-hematoma interface, and hematoma-brain interface. Specifically, FIG. 9A shows the shear wave particle velocity over time when a hematoma is present due to TBI. The graph shows weak reflection from skull-hematoma interface and then later emerging reflection of hematoma-brain interface. FIG. 9B, on the other hand, shows the shear wave particle velocity over time without a hematoma present. The graph shows strong reverberations that resonate between the skull exterior surface and skull-healthy brain interface.

Figure 9C:
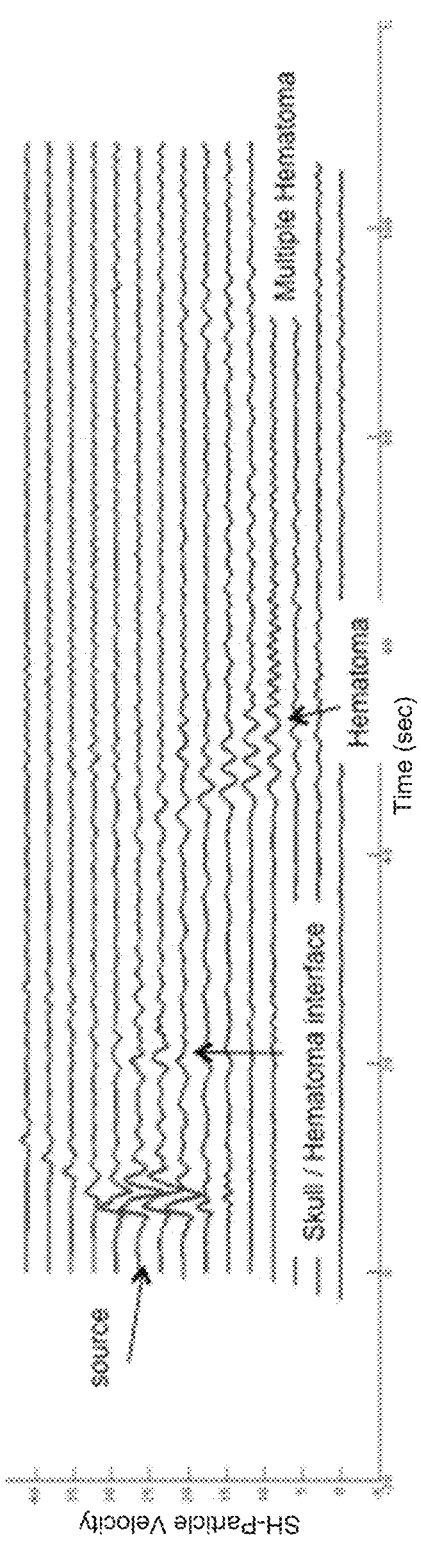
FIG. 9C is a graph showing the shear wave particle velocity as the shear waves are transmitted across the skull-brain interface and the effects of the hematoma over time.
Figure 9D:
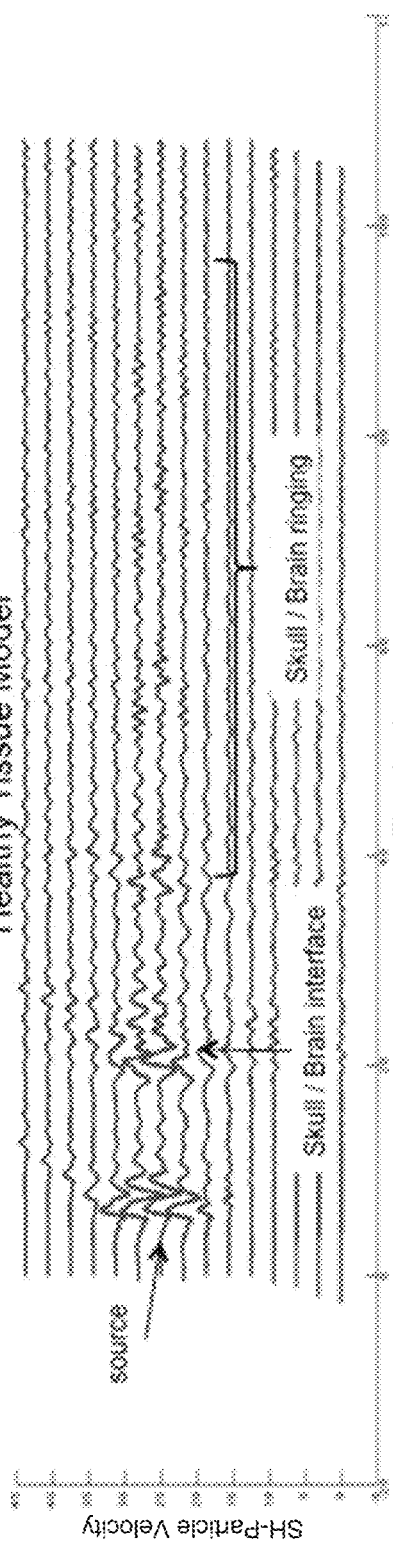
FIG. 9D is a graph showing the shear wave particle velocity as the shear waves are transmitted across the skull-brain interface and the effects of no hematoma present over time.

Similarly, FIGS. 9C and 9D show shear wave transmission across the skull bone and brain tissue in response to the ultrasonic signal input at the skull exterior surface. The graphs show the time series of the ultrasonic receiver array, positioned at the exterior of the skull, that records signal returns from the skull-brain interface, skull-hematoma interface, and hematoma-brain interface. Specifically, FIG. 9C shows the shear wave particle velocity over time when a hematoma is present due to TBI. The graph shows weak reflection from skull-hematoma interface and then later emerging reflection of hematoma-brain interface. FIG. 9B, on the other hand, shows the shear wave particle velocity over time without a hematoma present. The graph shows strong reverberations that resonate between the skull exterior surface and skull-healthy brain interface.

In one non-limiting example, a full finite difference scheme may be implemented into the system 10 to measure full elastic wave propagation in tissue and bone, for example. Particle velocity orientations may include longitudinal/compression (P), shear vertical (SV), and shear transverse (SH). The finite difference scheme may include a coupled wave equation to compute the stress tensor and resultant particle velocity (observed vibration) at every node. Particle velocity or displacement time series may be computed at skin surface nodes. In one embodiment, an alternating direction implicit (ADI) may be incorporated to allow large time jumps to speed the wave propagation simulation process up when needed. The scheme provides complex spatial images as a function of time to show the complex wave paths in the body. In use, horizontally polarized shear waves typically interfere the least with surface wave phenomena. This results in a more accurate, least distorted image as compared to conventional longitudinal waves (i.e., those used in common ultrasonic imaging practice). Thus, thin hematoma signatures, for example between about 1 mm and about 2 mm, may be observed that are positioned at the skull brain interface.

Figure 10:
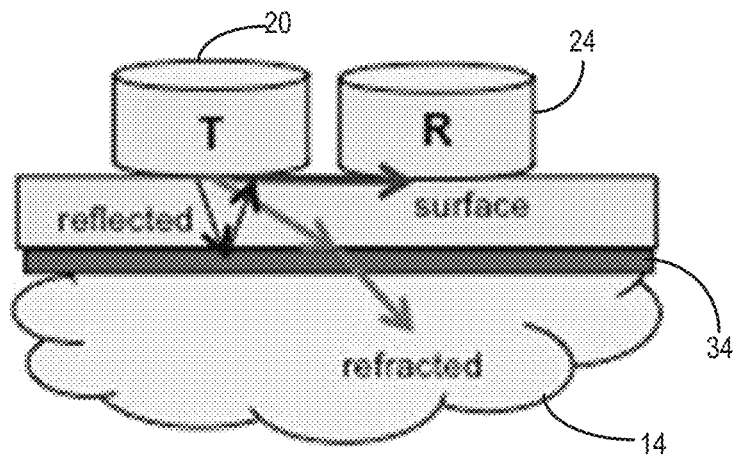
FIG. 10 is an image showing an exemplary bi-static measurement configuration for measuring surface wave transmission.

Turning now to FIG. 10, an exemplary ultrasonic wave excitation source 20 and receiver array 24 in a bi-static measurement configuration is shown. The bi-static measurement configuration may be used to estimate the reflection component from a direct transmission measurement. The direct transmission measurement may be combined with the measured surface wave to construct complete observed time series waveforms. For skull/brain TBI measurements, for example, the bi-static measurement configuration may include a two-step process. First, the direct transmission is measured across the skull 34 with and without the hematoma. Second, the surface wave is measured from the ultrasonic wave excitation source 20 (e.g., transducer) and receiver array 24. The complete time series waveform may be the sum of both the direct (estimated for 2 way travel and polarity) and the surface wave.

Figure 11A:
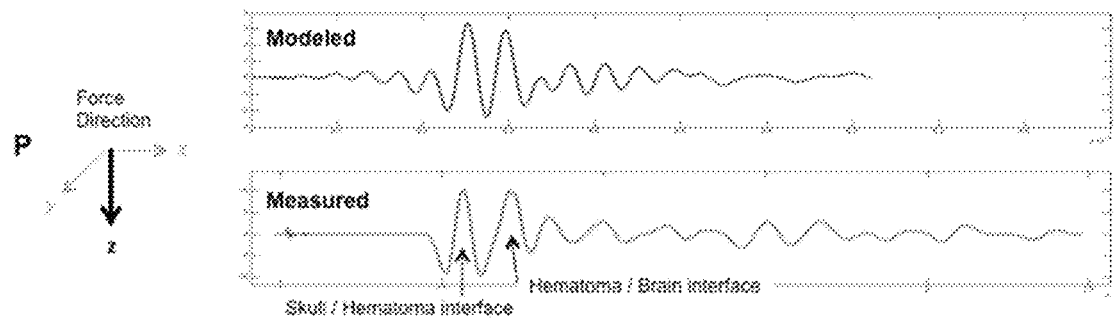
FIG. 11A are graphs showing modeled and measured time series data of reflection components in the brain tissue in longitudinal transmissions.
Figure 11B:
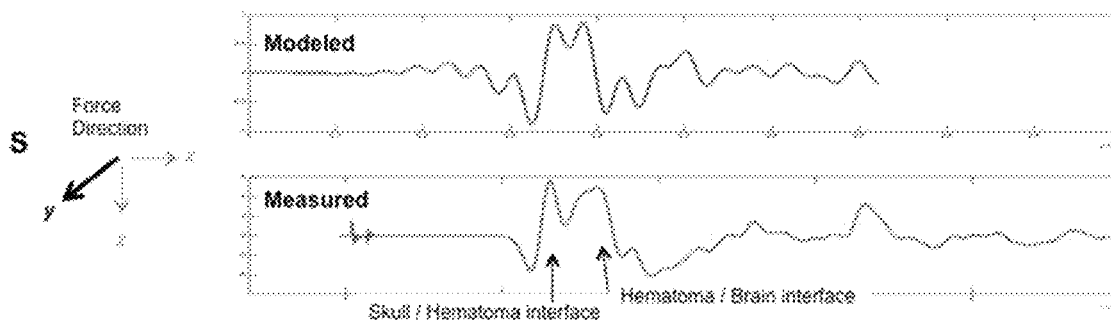
FIG. 11B are graphs showing modeled and measured time series data of reflection components in the brain tissue in shear transmissions.

The reflection wave components are shown in FIGS. 11A and 11B for the skull/hematoma/brain tissue configuration. The modeled time series is generated using the full finite difference model, as previously described. Longitudinal (P) and shear (S) transmissions are shown and compared in FIGS. 11A and 11B. The reflection wave components show the presence of the hematoma. The evidence of the hematoma is observed in the 'doublet' peak in the return from the skull/hematoma interface and hematoma/brain interface. Obtaining the subsurface reflection image of the hematoma may be challenging since, the surface wave signature combines and interferes with the reflection signature. The surface wave signature does not contain information pertaining to the hematoma, but only skull surface inhomogeneities. The surface wave thus distorts, contaminates and confuses the reflected wave signature. In many cases, the surface wave interference can partially or totally mask the reflection signature.

Figure 12:
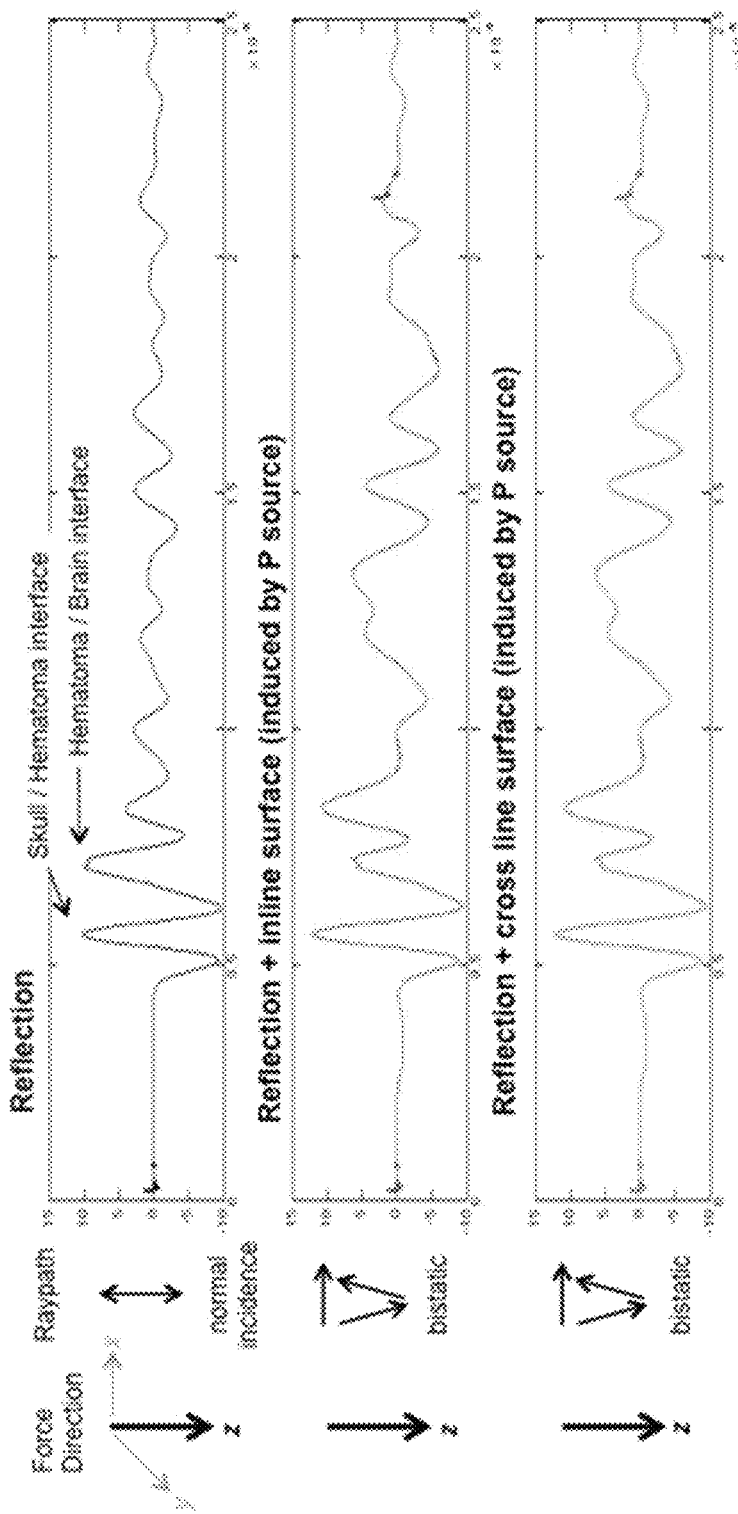
FIG. 12 are graphs showing measured time series signatures for shear waves in the brain tissue including reflection components induced by longitudinal sources.

For example, as shown in FIG. 12 measured time series signatures for P-waves in the skull/hematoma/brain phantom specimen configuration are shown. The top graph shows the desired reflection component from the hematoma. The bottom two graphs of FIG. 12 show the reflection combined with the surface wave signature contributions. Two surface wave orientations are shown that are 90 degrees apart. The reflection wave components of the top graph show the presence of the hematoma. The evidence of the hematoma is observed in the 'doublet' peak in the return from the skull/hematoma interface and hematoma/brain interface. The surface wave component introduces temporal structure and signature to the observed time series. Additional amplitude peaks and troughs are observed that confound the real geometry from the subsurface. These additional structures suggest other interfaces that appear to exist below the hematoma in the brain tissue itself. However, these signatures may cause false and incorrect interpretations of existing layers that do not exist below the hematoma into the brain. Moreover, the hematoma 'doublet' amplitude is diminished due to destructive surface wave interference. In addition, the surface wave component is independent of orientation where P-wave surface energy is spread omnidirectionally from the transmit transducer.

Figure 13:
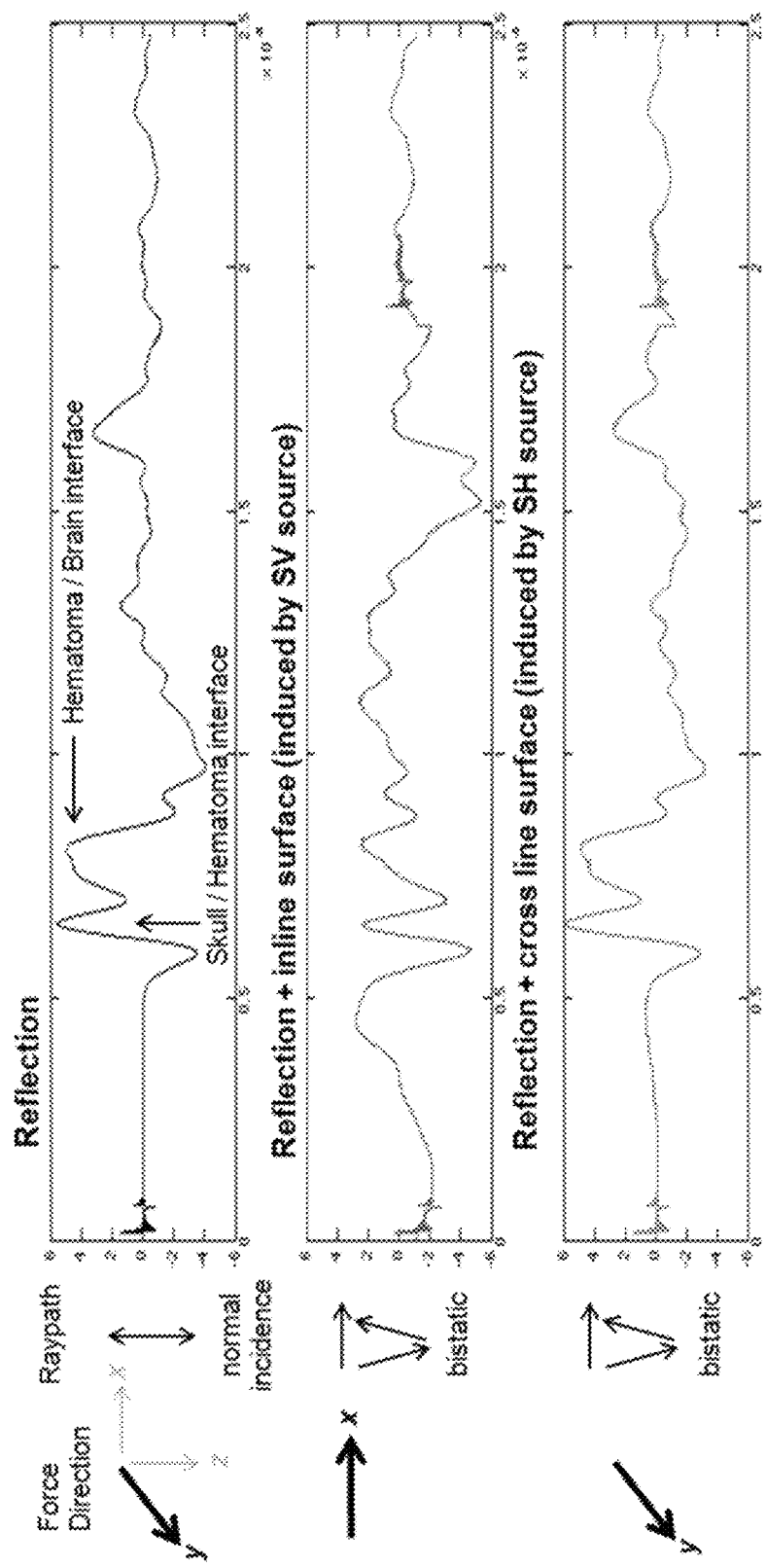
FIG. 13 are graphs showing measured times series signatures for shear waves in the brain tissue including reflection components induced by shear sources.

Alternatively, measured time series signatures for shear-waves in the skull/hematoma/brain phantom specimen configuration are shown in FIG. 13. The top graph shows the desired reflection component from the hematoma. The bottom two graphs of FIG. 13 show the reflection combined with the surface wave signature contributions. Two surface wave orientations are shown that are 90 degrees apart. The reflection wave components show the presence of the hematoma. The evidence of the hematoma is observed in the 'doublet' peak in the return from the skull/hematoma interface and hematoma/brain interface in the top graph. Two orientations are shown for the surface wave contributions: 1) inline, where the shear excitation force is in the direction of the receive transducer and 2) cross line, where the shear excitation force is transverse or 90 degrees to the receiver transducer.

In the case of the inline shear excitation shown in FIG. 13, the surface wave component introduces temporal structure and signature to the observed time series. Additional amplitude peaks and troughs are observed that confound the real geometry from the subsurface. These additional structures suggest other interfaces that appear to exist below the hematoma in the brain tissue itself. However, these signatures may cause false and incorrect interpretations of existing layers that do not exist below the hematoma into the brain. Moreover, the hematoma 'doublet' amplitude is diminished due to destructive surface wave interference.

In the case of the cross line shear excitation shown in FIG. 13, the surface wave component propagates in a line that is 90 degrees from the receive transducer orientation and position. Thus, minimal surface wave signals are observed at the measurement transducer. However, the down-going and up-going reflection components are received at the transducer. Thus, the transverse shear wave provides the least distortion and best representation of the subsurface structure.

Figure 14C:
FIG. 14C is an image showing shear wave transmission along the tibia leg bone without a stress fracture in response to an ultrasonic signal input exterior to the skin surface.
Figure 14B:
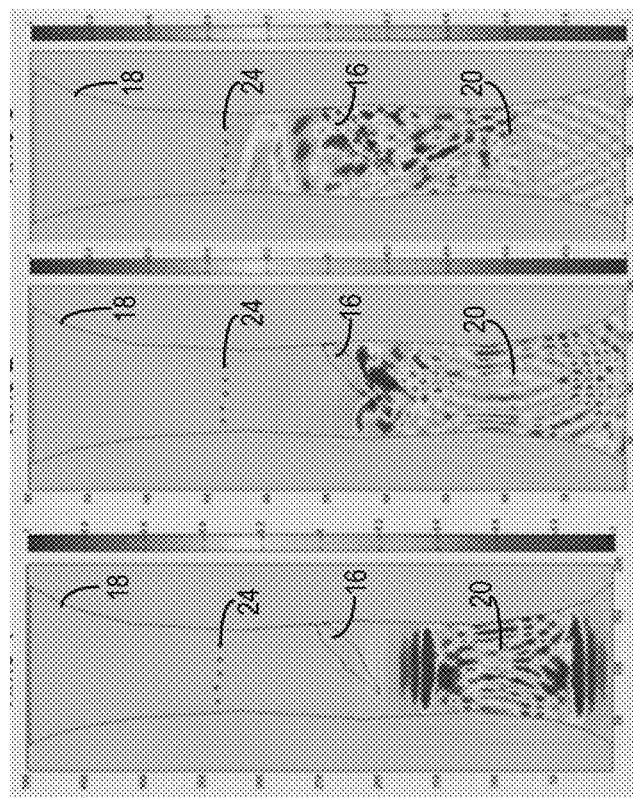
FIG. 14B is an image showing shear wave transmission along the tibia leg bone of FIG. 14A with a stress fracture in response to an ultrasonic signal input exterior to the skin surface.
Figure 14A:
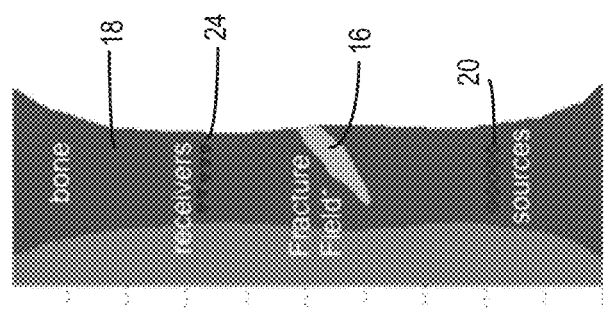
FIG. 14A is an image showing the system configured to implement the present disclosure for imaging the presence of a bone fracture in a tibia leg bone.

Turning now to FIG. 14A, an exemplary tibia leg bone 18 is shown with the presence of a fracture 16. The ultrasonic wave excitation source 20 and the ultrasonic receiver array 24 are shown positioned exterior to the skin around the bone 18. Shear waves are transmitted across the leg bone 18 in response to the ultrasonic signal input delivered by the ultrasonic wave excitation source 20. As shown in FIG. 14B, shear wave transmission across leg bone 18 in response to the ultrasonic signal input over time shows significant shear wave distortion and attenuation as it travels through the fracture 16 from time 1 to time 3. FIG. 14C, on the other hand, shows the shear wave front due to no fracture in its path, exhibiting little distortion and attenuation in comparison to the bone 18, shown in FIG. 14B containing the fracture 16.

Figure 15A:
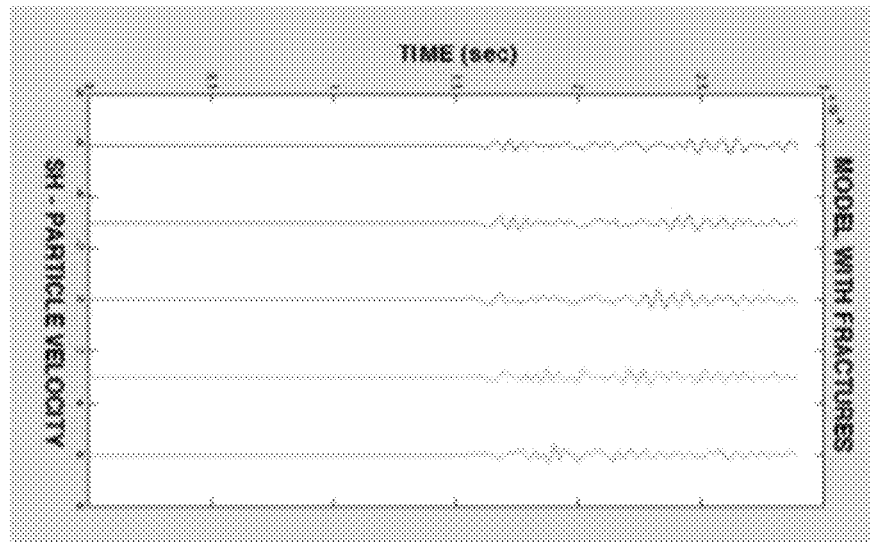
FIG. 15A is a graph showing the shear wave particle velocity as the shear waves are transmitted across the tibia leg bone of FIG. 8B and the effects of the stress fracture over time.
Figure 15B:
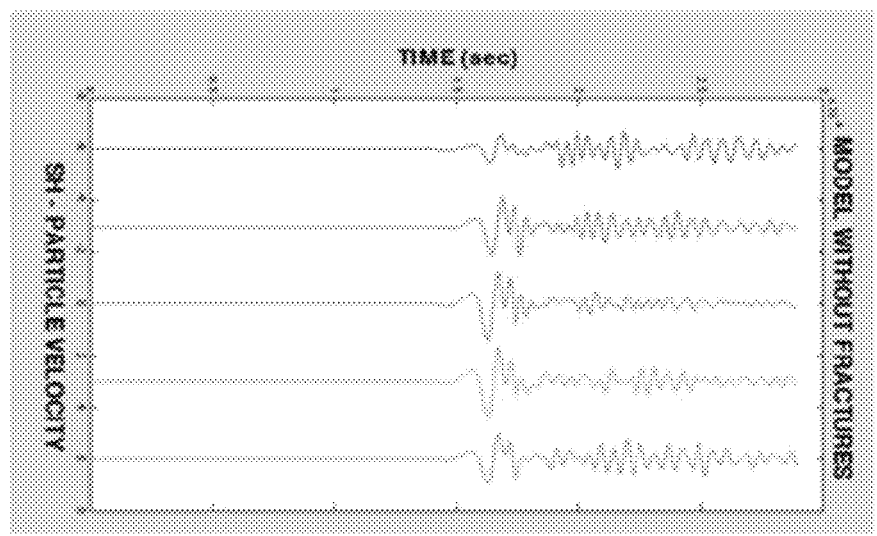
FIG. 15B is a graph showing the shear wave particle velocity as the shear waves are transmitted across the tibia leg bone of FIG. 14C and the effects of no stress fracture over time.

FIGS. 15A and 15B show shear wave transmission across the tibia leg bone in response to the ultrasonic signal input exterior to the leg bone. The graphs show the time series of the ultrasonic receiver array that records signal arrivals from the ultrasonic wave excitation source from an offset distance relative to the ultrasonic receiver array. Specifically, FIG. 15A shows the shear wave particle velocity over time when a fracture is present. The graph shows weak signal transmission across the fracture and attenuated signal received at the ultrasonic receiver array. FIG. 15B, on the other hand, shows the shear wave particle velocity over time without a fracture present. The graph shows strong signal transmission received at the offset ultrasonic receiver array compared to FIG. 15A.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for determining changes in tissue, the method comprising the steps of:
   a) directing horizontally-polarized shear waves at a tissue by applying a shear excitation force to a surface of the tissue using an ultrasonic wave excitation source positioned about the surface of the tissue such that the shear waves propagate in the tissue, wherein the horizontally-polarized shear waves propagate in a direction perpendicular at least to a propagation direction of surface waves induced by the ultrasonic wave excitation source;
   b) using an ultrasonic receiver configured to detect the horizontally-polarized shear waves, wherein said using the ultrasonic receiver comprises positioning and orienting the ultrasonic receiver about the surface of the tissue and detecting at least a portion of the horizontally-polarized shear waves, wherein the ultrasonic receiver is positioned and oriented relative to the ultrasonic wave excitation source to reduce interference from an inline configuration of the ultrasonic receiver and the ultrasonic wave excitation source with the surface waves propagating in the tissue;
   c) estimating, using the detected horizontally-polarized shear waves, a shear-wave dispersion in the tissue that represents variation in the velocity of the horizontally-polarized shear waves as a function of frequency of the horizontally-polarized shear waves; and
   d) generating a report indicative of tissue health based on a difference between the estimated shear-wave dispersion as compared with a reference shear-wave dispersion.

2. The method as recited in claim 1, wherein step b) includes measuring amplitude and phase variations of the detected horizontally polarized shear waves.

3. The method as recited in claim 1, wherein the ultrasonic wave excitation source and the ultrasonic receiver are oriented cross line to mitigate interference from the surface waves traveling along the surface of the tissue.

4. The method as recited in claim 1, further comprising:
   estimating viscosity and/or mass in the tissue based on the estimated shear-wave dispersion,
   comparing the estimated viscosity and/or the estimated mass to a reference viscosity and/or a reference mass respectively, and
   including information about the comparison of the estimated viscosity and/or the estimated mass to the reference viscosity and/or reference mass respectively on the report.

5. The method as recited in claim 4, wherein the tissue is a brain, and wherein, when the estimated viscosity in the tissue is larger than the reference viscosity, the report is generated to indicate a likelihood of a brain hematoma.

6. The method as recited in claim 1, wherein the tissue health includes at least one of a likelihood of traumatic brain injury, stress induced fracturing, and internal bleeding of the tissue.

7. The method as recited in claim 1, wherein the ultrasonic wave excitation source is configured to apply the shear excitation force to the tissue without contacting the tissue, and wherein the ultrasonic receiver is configured to detect the horizontally-polarized shear waves from the tissue without contacting the tissue.

8. The method as recited in claim 1, wherein the ultrasonic wave excitation source includes a plurality of piezoelectric transducers configured to generate the horizontally-polarized shear waves that propagate in a direction transverse to the orientation of the ultrasonic receiver and to generate compressional waves that propagate in a vertical direction in the tissue.

9. The method as recited in claim 1, wherein the ultrasonic receiver of step b) includes a laser vibrometer configured to detect the horizontally-polarized shear waves by measuring, without contacting the tissue, surface vibrations of the tissue induced by the horizontally-polarized shear waves.

10. The method as recited in claim 9, wherein the surface vibrations modulate a laser receiver carrier and causes a Doppler shift as the exterior of the tissue vibrates towards and away from the laser vibrometer, the Doppler shift providing a vibration frequency while an excursion across a number of wavelengths on the laser receiver carrier provides a signal amplitude.

11. The method as recited in claim 1, further including performing adaptive beam forming signal processing to improve at least one of image signal to noise ratio, travel speed variations, and attenuation.

12. The method of claim 1, wherein the ultrasonic wave excitation source is positioned to direct generated waves at a skull exterior surface, and wherein the horizontally polarized shear waves generated by the ultrasonic wave excitation source are transmitted across a skull bone and into brain tissue.

13. The method of claim 12, wherein the difference between the estimated shear-wave dispersion as compared with the reference shear-wave dispersion is used to detect a hematoma under the skull exterior surface.

14. The method of claim 1, wherein the difference between the estimated shear-wave dispersion as compared with the reference shear-wave dispersion is used to detect coagulating blood in the tissue through which the shear waves propagated.

15. The method of claim 1, wherein the ultrasonic wave excitation source and ultrasonic receiver are arranged such that, when the horizontally-polarized shear waves are generated externally to a skull bone of a subject and directed at the skull bone, the horizontally-polarized shear waves propagate through the skull bone and into brain tissue.

16. A system for determining changes in tissue, the system comprising:
   an ultrasonic wave excitation source configured to be positioned about a surface of the tissue and generate horizontally-polarized shear waves in the tissue by applying a shear excitation force to the surface of the tissue;
   an ultrasonic receiver configured to be positioned about the surface of the tissue and detect the horizontally-polarized shear waves from the tissue, wherein the ultrasonic receiver is oriented relative to the ultrasonic wave excitation source to reduce interference from an inline configuration of the ultrasonic receiver and the ultrasonic wave excitation source with compressional and surface waves induced in the tissue by the ultrasonic wave excitation source;
   a processor and memory having instructions that, when executed by the processor, carry out steps of:
      i) controlling the ultrasonic wave excitation source to direct the horizontally-polarized shear waves in the tissue, wherein the horizontally-polarized shear waves propagate in a direction perpendicular at least to a propagation direction of the surface waves induced by the ultrasonic wave excitation source;

ii) using the ultrasonic receiver to detect the horizontally-polarized shear waves;

iii) estimating, using the detected horizontally-polarized shear waves, a shear-wave dispersion in the tissue that represents variation in the velocity of the horizontally-polarized shear waves as a function of frequency of the horizontally-polarized shear waves; and iv) generating a report indicative of tissue health based on a difference between the estimated shear-wave dispersion as compared with a reference shear-wave dispersion.

17. The system as recited in claim 16, wherein the processor further carries out a step of measuring amplitude and phase variations of the detected horizontally-polarized shear waves.

18. The system as recited in claim 16, wherein the report indicates a likelihood of at least one of traumatic brain injury, stress induced fracturing, and internal bleeding of the tissue based on the difference between the estimated shear-wave dispersion as compared with the reference shear-wave dispersion.

19. The system as recited in claim 16, wherein the ultrasonic receiver includes a laser vibrometer configured to measure surface vibrations induced by the ultrasonic wave excitation source.

20. The system as recited in claim 19, wherein the laser vibrometer includes a laser spot size adjustable to about 1 millimeter in diameter, thereby providing a spatial resolution of about 1 millimeter.

21. The system as recited in claim 16, wherein the processor further carries out the steps of estimating viscosity and/or mass in the tissue based on the estimated shear-wave dispersion, comparing the estimated viscosity and/or the estimated mass to a reference viscosity and/or a reference mass respectively, and including information about the comparison of the estimated viscosity and/or the estimated mass to the reference viscosity and/or the reference mass respectively on the report to indicate health of the tissue through which the horizontally-polarized shear waves propagated.

22. The system of claim 16, wherein the ultrasonic wave excitation source and the ultrasonic receiver are arranged such that, when the horizontally-polarized shear waves are generated externally to a skull bone of a subject and directed at the skull bone, the horizontally-polarized shear waves propagate through the skull bone and into brain tissue.

* * * * *